(12) United States Patent
Shami

(10) Patent No.: US 7,638,117 B2
(45) Date of Patent: Dec. 29, 2009

(54) HAIR TRANSFORMATION METHOD

(75) Inventor: Farouk Shami, The Woodlands, TX (US)

(73) Assignee: Farouk Systems, Inc., Houston, TX (US)

( * ) Notice: Subject to any disclaimer, the term of this patent is extended or adjusted under 35 U.S.C. 154(b) by 344 days.

(21) Appl. No.: 10/353,688

(22) Filed: Jan. 29, 2003

(65) Prior Publication Data

US 2004/0146476 A1 Jul. 29, 2004

(51) Int. Cl.
*A61Q 5/04* (2006.01)
(52) U.S. Cl. .................. 424/70.2; 132/206
(58) Field of Classification Search .......... None
See application file for complete search history.

(56) References Cited

U.S. PATENT DOCUMENTS 4,871,535 A * 10/1989 Helioff et al. ............. 424/70.2
5,352,443 A * 10/1994 Kubo et al. ................ 424/70.2
6,125,856 A   10/2000 Yamashita

FOREIGN PATENT DOCUMENTS

EP  1 117 112   * 1/2002
GB  2197352     * 5/1988

OTHER PUBLICATIONS

The Science Of Hair Care by Zviak, pp. 2-11 (1986).*

* cited by examiner

*Primary Examiner*—Jyothsna A Venkat
(74) *Attorney, Agent, or Firm*—Greenberg Traurig LLP

(57) ABSTRACT

Disclosed is a method and composition for transforming hair. The composition is a dual composition that is useful to curl or straighten hair. The composition also repairs hair. The reducing solution includes monoethanolamine and thioglycolic acid and is essentially ammonium hydroxide free.

14 Claims, No Drawings

HAIR TRANSFORMATION METHOD

BACKGROUND OF THE INVENTION

1. Field of the Invention

A new and improved method and formulation to permanently transform curly and frizzy hair to smooth, straight, silky hair. The same formulation can be used also to transform straight hair to curly or wavy hair. This permanent transformation method can help to improve and repair hair condition, texture and strength. The same method can be used to repair and reconstruct hair structure.

2. Description of the Prior Art

Techniques for curling, waving and straightening hair have existed since the earliest times. Egyptian women, and later Roman and Grecian women, used wet mud to achieve desired results. However, these results were not long lasting. Around 1924, ammonium hydroxide in combination with borax was introduced for longer lasting styles that would maintain the desired shape through several washings. Also in the 1920's, chemical methods, including cold waves and heating methods, were introduced to the field.

Hair's natural shape is determined genetically during a keratinization stage. The hair follicle wall shapes cells that are produced by hair papilla. These cells are converted into a hard keratin making it difficult to alter the characteristic structure.

Any process of curling, waving or straightening hair involves a transformation method in which the hair keratin is softened, reshaped to the desired form or shape, then rehardened to the new desired shape.

Permanent softening of hair involves the breaking or disruption of keratin disulphide bonds or linkages. This mechanism occurs when hair is treated with an alkali or reducing agent. The amount of softening depends on the strength and concentration of the reducing agent compound, length of time the compound is left in contact with hair, temperature and amount of stress applied to hair during such process.

After the reduction treatment of disulphide linkage, it is necessary to reharden the hair structure into the new shape or desired form through an oxidation process. Hair reoxidation cross-links the disulphide linkage or bonds from keratocysteine to keratocystine thereby restoring the mechanophysical properties of hair. In this manner, sulphide-reduced hair can be transformed and rehardened by the action of hydrogen peroxide.

Methods currently used to transform hair cause permanent damage to the hair. These methods over-dry and weaken the structure of hair leaving the hair unhealthy and without shine. Therefore, it would be advantageous to introduce a method and formulation that permanently restructures and bond the hair without causing damage. It would be equally advantageous to introduce a method and formulation that acts to repair damage to hair while transforming hair. Current methods also require one formulations specific to curl or wave hair and another formulation to straighten hair. Be advantageous to perform either of these actions with one formulation.

Many current hair transformation formulations require ammonia or ammonium hydroxide as an ingredient. Ammonia compounds and the gases that evolve therefrom are hazardous for the health, unpleasant to smell and harsh to hair. The combination of ammonium hydroxide with other substances increases the harmful emissions. For example, the combination with thioglycolic acid produces an acrid odor. It would be advantageous for a hair transformation formulation to be substantially free from ammonia compounds.

As noted above, many conventional methods apply the basic softening compound on an open hair cuticle and/or with the cuticle raised. This can result in uneven and fast absorption leading to damage and dryness. It would be advantageous to close the hair cuticle prior to the application of a basic softening compound.

Conventional methods of curling include tedious rolling of hair onto curlers, application of basic solution to rolled hair, followed by neutralization. The requirement of rolling in advance to gain the desired shape is time-consuming and can stress the hair and scalp. It would therefore be advantageous to create the desired shape after the hair is softened. It would be advantageous to create this shape through the use of a tool that allows for short applications of heat.

BRIEF SUMMARY OF THE INVENTION

In accordance with the invention, one or more of the foregoing advantages are achieved through a method of repairing hair and altering the shape of hair by applying a cationic acid solution to hair as a first acid application. Preferably, the hair is moistened prior to the application of the cationic acid solution. The amount of the cationic acid solution to be applied in the first application is effective to at least partially close the hair cuticle and to lower the pH of the hair to between about 3 and 4. A cationic reducing composition is applied to the hair while the first acid application remains in the hair. The cationic reducing composition is maintained for a period of time sufficient to reduce the hair into a soft and structurally-receptive condition. In an alternate embodiment, the hair is heated with the reducing composition in place. The hair is rinsed to remove substantially all cationic acid solution and cationic reducing composition when the structurally-receptive condition has been reached. This substantially halts or arrests further reduction of the hair.

The cationic acid solution is applied to the hair in a second acid application and the hair is at least partially dried with the second application remaining in the hair. The hair is formed into a pre-selected shape and is neutralized through the addition of neutralizer solution to harden the pre-selected shape.

In a preferred embodiment, the cationic acid solution includes hydrolyzed silk, a weak organic acid in aqueous solution. Preferred weak organic acids include citric acid, acetic acid, mixtures of citric and acetic acid and the like. Other preferred embodiments include the addition of vegetable proteins and/or wheat proteins.

The cationic reducing composition of the invention includes monoethanolamine and thioglycolic acid. Additional preferred components of the cationic reducing composition include hydrolyzed silk protein and oil.

To further enhance the condition of the hair being transformed, the cationic acid solution is applied to the neutralized hair in a third acid application. In a preferred embodiment, an application of an emulsifier containing cationic silk is made to the neutralized hair. The hair is then at least partially dried.

While a variety of methods or tools can be used to form the hair into the pre-selected shape, a ceramic hair iron is particularly useful.

In accordance with the invention, a hair transformation solution for softening hair bonds is disclosed. The preferred compounds in the hair transformation solution include monoethanolamine, thioglycolic acid, and silk proteins. Additional compounds, such as oil, are also desirable in some embodiments. While other compounds can also be added for desired effects, ammonium hydroxide is avoided resulting in a transformation solution that is essentially free from ammonium hydroxide. After the use of the hair transformation solution of the invention or other hair transformation solutions, a hair neutralization formulation is needed. The hair neutralization formulation of the invention includes hydrogen peroxide and silk.

DETAILED DESCRIPTION OF THE INVENTION

The hair transformation or repair method of the current invention typically includes a first step of washing the hair to remove impurities and excess oils. The hair is well-rinsed and then toweled dry so that excess moisture is removed. The first cationic solution is applied to the hair to fill voids and close the hair cuticle by lowering pH, in a preferred embodiment, to 3-4. In a preferred embodiment, the first cationic solution remains in the hair during the application of the cationic reducing composition. The cationic reducing composition is preferably brushed into the hair, such as with a color brush. The reducing composition remains in the hair until the structure of the hair is softened to the stage where is can be permanently curled or straightened. In a preferred embodiment, the hair is covered with a plastic cap. Warmth is applied such as through the use of a blow dryer, hooded dryer, heat lamps or the like. This process proceeds from about 5 to 20 minutes or until the hair is processed. The cap is removed and the hair is cooled for about 5 to 10 minutes or until hair is reduced into a soft structure ready to accept a new shape. After the reducing composition has been applied to the hair for an amount of time sufficient to transform the hair, the hair is thoroughly rinsed with warm water to stop the action of the reduction of the hair. The hair is then towel dried to remove excess moisture.

The same cationic acid leave-in solution is applied in a second application. This allows a low pH to be maintained to reduce potential damage to the hair. After application of the cationic acid solution, the hair is blown dry without removal of the cationic acid solution. This typically removes 80-90% of the water. The dry hair is pressed into the pre-selected desired shape, preferably through the use of a ceramic hot iron. The flat ceramic iron is used to press hair straight or curly into the form or shape desired. The size of the curling ceramic irons roundness determines the size of the curl to be transformed. When the hair is formed into the desired shape, the hair is neutralized to harden the hair into the new transformed shape. The neutralizing solution can be applied with a tint brush, from a spray bottle or by other means effective to neutralize the hair. Neutralization is preferable accomplished using a hydrogen peroxide solution. To improve conditioning, the hydrogen peroxide solution is preferably infused with silk proteins. The neutralization solution is left in the hair for 5-10 minutes or for an amount of time sufficient to neutralize the hair. The neutralization solution is then rinsed and the hair is towel dried. In one preferred embodiment, a moisturizing conditioner is applied to the hair for 5 minutes after the previous process is complete. This enhances hair condition and moisture. The hair is then rinsed to generally remove the conditioner from the hair and toweled dry. In a preferred embodiment, a third application of the same cationic acid solution is applied. The multiple applications of cationic acid solution are preferred, but not required, as a means to maintain a low pH to reduce any possibility of damage to the hair. Silicone is useful in the cationic solution. This cationic acid solution can remain in the hair while the hair is blown dry and styled.

In a preferred embodiment, the reducing composition contains silk, wheat proteins, oils, extracts and emulsifiers. The silk is preferably in the form of hydrolyzed silk proteins in solution. Wheat proteins are typically in the form of liquid. Exemplary oils useful in this mixture are olive oil, canola oil, safflower oil and other vegetable oils. Preferred extracts include sage, chamomile, and thyme. Emulsifiers are used for the purpose of creating a stable solution. While emulsifiers known in the industry are useful, preferred emulsifiers include fatty alcohols and polyethylene glycol ether of cet-earyl alcohol.

One preferred reducing composition includes the following formulation, on a weight basis:

| Water | 50-75% |
|---|---|
| Emulsifiers | 10-20% |
| Oil | 2-10% |
| Silk Proteins | 2-10% |
| Wheat Proteins | 2-10% |
| Monoethanolamine | 2-10% |
| Thioglycolic acid | 10-25% |

This solution is cationic.

The cationic acid solution of the invention contains silk, wheat, proteins and emulsifiers.

One preferred cationic acid solution includes the following formulation:

| Water | 90.0-92.0% |
|---|---|
| Quats | 0.5-1.5% |
| Silk Protein | 0.2-2.0% |
| Wheat Proteins | 1.0-2.5% |
| Other | 5.0-7.0% |

The preferred embodiment of the invention includes the use of a novel cationic acid solution formulation to maximize positive effects and benefits to the hair. The preferred embodiment also uses the novel cationic reducing composition formulation. The neutralizer useful in the method of the invention can be any neutralizer useful to neutralize the hair. While hydrogen peroxide is useful, other neutralizers will be known to those with skill in this art. The novel neutralizing solution of hydrogen peroxide with silk proteins provides additional benefits.

The moisturizer used in a preferred embodiment of this invention can be any moisturizer known to those in the art. One preferred moisturizer includes cationic silk and wheat, such as the product sold by Farouk Systems under the trademark of Moisturize & Shine. While any device known in the art can be used to change the form of the hair, such as by curling or straightening, a preferred embodiment includes the use of a ceramic iron. The use of a ceramic iron provides benefits over traditional rollers or metal irons, but such curling/straightening devices and the like are also encompassed within this invention.

A ceramic dryer is also preferred in that ceramic heat keeps moisture in the hair unlike copper or other metal-generated heat, which tends to dry moisture. Ceramic heat that produces infra red and ionic charges dries hair faster and smoother.

Notably, the cationic acid solution and the reducing composition can be used to both straighten and curl hair. This dual functionality of the straightening/curling formulations is novel.

While the present invention has been described and/or illustrated with particular reference to a method and formulation for transforming hair, it is noted that the scope of the present invention is not restricted to the particular embodiment(s) described. It should be apparent to those skilled in the art that the scope of the invention can include the use of various additional steps that have a positive impact on hair quality or transformation as well as additional components in the formulations. Moreover, those skilled in the art will appreciate that the invention described above is susceptible to variations and modifications other than those specifically described. It is understood that the present invention includes all such variations and modifications, which are within the spirit and scope of the invention. It is intended that the scope of the invention not be limited by the specification, but be defined by the claims set forth below.

It is claimed:

1. A method of altering the shape of hair comprising the steps of:
    applying a cationic acid solution to moist hair as a first acid application, the amount of the first application being effective to lower the pH of the hair to between about 3 and 4;
    applying a cationic reducing composition while the first acid application remains in the hair, the cationic reducing composition being maintained for a period of time sufficient to reduce the hair into a structurally-receptive condition;
    rinsing the hair to remove substantially all cationic acid solution and cationic reducing composition so that further reduction of the hair is substantially arrested;
    applying the cationic acid solution in a second acid application;
    at least partially drying the hair with the second application;
    forming the hair with the second application into a pre-selected shape; and
    neutralizing the hair with neutralizer solution to harden the pre-selected shape.

2. The method of claim 1 wherein the cationic acid solution comprises:
    hydrolyzed silk; and
    a weak organic acid in aqueous solution.

3. The method of claim 2 wherein the weak organic acid is selected from the group consisting of citric acid, acetic acid and mixtures thereof.

4. The method of claim 1 wherein the cationic reducing composition comprises:
    monoethanolamine; and
    thioglycolic acid.

5. The method of claim 4 wherein the cationic reducing composition further comprises:
    hydrolyzed silk; and
    oil.

6. The method of claim 1 further comprising the step of: applying the cationic acid solution to the neutralized hair in a third acid application.

7. The method of claim 1 wherein a ceramic hair iron is used to form the hair into the pre-selected shape.

8. The method of claim 1 further comprising adding heat to the hair after the cationic reducing composition has been applied.

9. The method of claim 1 wherein the method is performed in the absence of ammonia hydroxide.

10. The method of claim 1, wherein the hair cuticle is partially closed upon the application of the cationic acid solution as a first acid application.

11. The method of claim 1, wherein the method can be utilized for both straightening and curling hair.

12. The method of claim 1, further comprising adding heat to the hair while the cationic reducing composition is in the hair.

13. The method of claim 5, wherein the oil is selected from the group consisting of olive oil, canola oil, safflower oil and vegetable oil.

14. The method of claim 1, wherein the first acid application maintains the pH of the hair to between 3 and 4.

* * * * *

UNITED STATES PATENT AND TRADEMARK OFFICE
CERTIFICATE OF CORRECTION

| | |
|---|---|
| PATENT NO. | : 7,638,117 B2 |
| APPLICATION NO. | : 10/353688 |
| DATED | : December 29, 2009 |
| INVENTOR(S) | : Farouk Shami |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 912 days.

Signed and Sealed this

Ninth Day of November, 2010

David J. Kappos
*Director of the United States Patent and Trademark Office*